United States Patent
Naidu et al.

(10) Patent No.: US 10,292,678 B2
(45) Date of Patent: May 21, 2019

(54) REAL-TIME IMAGE BASED RISK ASSESSMENT FOR AN INSTRUMENT ALONG A PATH TO A TARGET IN AN OBJECT

(71) Applicant: Analogic Corporation, Peabody, MA (US)

(72) Inventors: Ram Naidu, Newton, MA (US); Jason Plante, Chardon, OH (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 14/862,727

(22) Filed: Sep. 23, 2015

(65) Prior Publication Data

US 2017/0084022 A1   Mar. 23, 2017

(51) Int. Cl.
*G06T 7/00* (2017.01)
*A61B 8/08* (2006.01)
(Continued)

(52) U.S. Cl.
CPC ........... *A61B 8/0841* (2013.01); *A61B 8/463* (2013.01); *A61B 8/5223* (2013.01); *A61B 34/10* (2016.02);
(Continued)

(58) Field of Classification Search
None
See application file for complete search history.

(56) References Cited

U.S. PATENT DOCUMENTS 6,390,097 B1 * 5/2002 Chandra ............. G06F 19/3437
128/898
2007/0244387 A1 * 10/2007 Rodriguez Ponce .......................
G06F 19/321
600/411
(Continued)

FOREIGN PATENT DOCUMENTS

WO   WO 2016195698 A1 * 12/2016   ........... G06K 9/3233

OTHER PUBLICATIONS

Chen, Ken, et al. "Three dimensional ultrasound guided percutaneous renal puncture: A phantom study." Proceedings of 2012 IEEE-EMBS International Conference on Biomedical and Health Informatics. IEEE, 2012.*

(Continued)

*Primary Examiner* — Vu Le
*Assistant Examiner* — Tracy Mangialaschi
(74) *Attorney, Agent, or Firm* — TraskBritt

(57) ABSTRACT

A method includes receiving an intra-procedure image of a region of interest of an object. The intra-procedure image includes a representation of an instrument in the object. The method further includes identifying a location of the instrument in the object in the intra-procedure image. The method further includes combining the intra-procedure image with a pre-procedure image of the region of interest. The pre-procedure image includes a planned trajectory for the instrument from a surface of the object to a target in the object and segmented structure(s) to be avoided by the instrument during the procedure. The method further includes segmenting the same structure(s) in the intra-procedure image relative to the instrument using the segmented structure(s) in the pre-procedure image. The method further includes computing a risk of the instrument contacting the structure(s) along
(Continued)

the trajectory with the identified location, the trajectory, and the segmented structure(s) in the intra-procedure image.

20 Claims, 3 Drawing Sheets

(51) Int. Cl.
*A61B 8/00* (2006.01)
*A61B 34/10* (2016.01)

(52) U.S. Cl.
CPC ....... *A61B 8/5261* (2013.01); *A61B 2034/107* (2016.02)

(56) References Cited

U.S. PATENT DOCUMENTS

2009/0259230 A1* 10/2009 Khadem ............ A61B 19/5244
                                                    606/130
2014/0073907 A1*  3/2014 Kumar .................. A61B 10/00
                                                    600/414

OTHER PUBLICATIONS

Warfield, Simon K., et al. "Intraoperative segmentation and non-rigid registration for image guided therapy." International Conference on Medical Image Computing and Computer-Assisted Intervention. Springer, Berlin, Heidelberg, 2000.*

* cited by examiner

REAL-TIME IMAGE BASED RISK ASSESSMENT FOR AN INSTRUMENT ALONG A PATH TO A TARGET IN AN OBJECT

TECHNICAL FIELD

The following generally relates to an imaging and more particularly to real-time image based risk assessment for an instrument along a path to a target in an object, and is described with particular application to ultrasound imaging, but is also amenable to other imaging modalities.

BACKGROUND

Imaging has been used to guide procedures such as biopsies, resections, cryotherapy, ablations, etc. For instance, cancerous tumors have been treated using a needle that is inserted into the tumor, where the needle is used to ablate a region around a tip of the needle. The insertion of the needle to the tumor has been guided with an image. For example, the physician first views the image to determine how far the needle should travel and an appropriate trajectory by eye before the treatment commences. During the procedure, the clinician cognitively assess a risk of injury to neighboring anatomical structures such as the lungs, heart and other organs or major blood vessels as the needle is advanced to the target tissue along the trajectory. Unfortunately, due to a variety of factors including patient motion and needle deflection, it may be difficult for the clinician to determine if the needle is coming close to any of the neighboring anatomical structures solely based on the cognitive assessment as the needle is advanced. Furthermore, the clinician may have to advance the needle in small incremental steps and continuously review and interpret the image, which is a tedious and time consuming process that may increase in overall time, radiation dose when under X-ray guidance and cost of the procedure.

SUMMARY

Aspects of the application address the above matters, and others.

In one aspect, a method includes receiving an intra-procedure image of a region of interest of an object. The intra-procedure image includes a representation of an instrument in the object. The method further includes identifying the location of the instrument in the object in the intra-procedure image. The method further includes combining the intra-procedure image with a pre-procedure image of the region of interest of the object. The pre-procedure image includes a planned trajectory for the instrument from a surface of the object to a target in the object and segmented structure(s) to be avoided by the instrument during the procedure. The method further includes segmenting the same structure(s) in the intra-procedure image relative to the instrument using the segmented structure(s) in the pre-procedure image from the combined images. The method further includes computing a risk of the instrument contacting the structure(s) along the trajectory with the identified location of the instrument, the trajectory, and the segmented structure(s) in the intra-procedure image. The method further includes presenting the risk.

In another aspect, an apparatus includes an instrument identifier that receives a real-time image generated during a procedure and identifies a position of an instrument in the real-time image. The apparatus further includes a segmentor that segments a predetermined set of structures in the real-time image using previously segmented structure in a previously generated image. The apparatus further includes a risk assessor that computes a risk of the instrument damaging the structures from the identified position, the segmented structures in the real-time image, and a planned path for the instrument in the previously generated image. The apparatus further includes a plan evaluator that evaluates the plan using the computed risk and presents information indicating the risk along the planned path.

In another aspect, a non-transitory computer readable medium is encoded with computer executable instructions, which, when executed by a computer processor, causes the processor to: determine a location of a needle in an object in an intra-procedure image, fuse the intra-procedure image with a pre-procedure image, segment structure in the intra-procedure image with structure previously segmented in the pre-procedure image, and determine a risk of the needle coming into contact with the structure based on a pre-planned needle path to tissue of interest in the object, the location of the needle, and the segmented structure in the intra-procedure image.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

The following describes an approach for assessing risk of contact of an instrument with structure(s) in an object, during a procedure in which the instrument is advanced in the object to a target destination, based on segmentation and tracking of objects using feedback based on analysis of real-time images. By non-limiting example, this includes assessing a risk of damage to an anatomical structure located in a vicinity of a needle trajectory as the needle is guided towards target tissue of interest such as a lesion or tumor during an image guided procedure and also when the treatment is performed.

Figure 1:
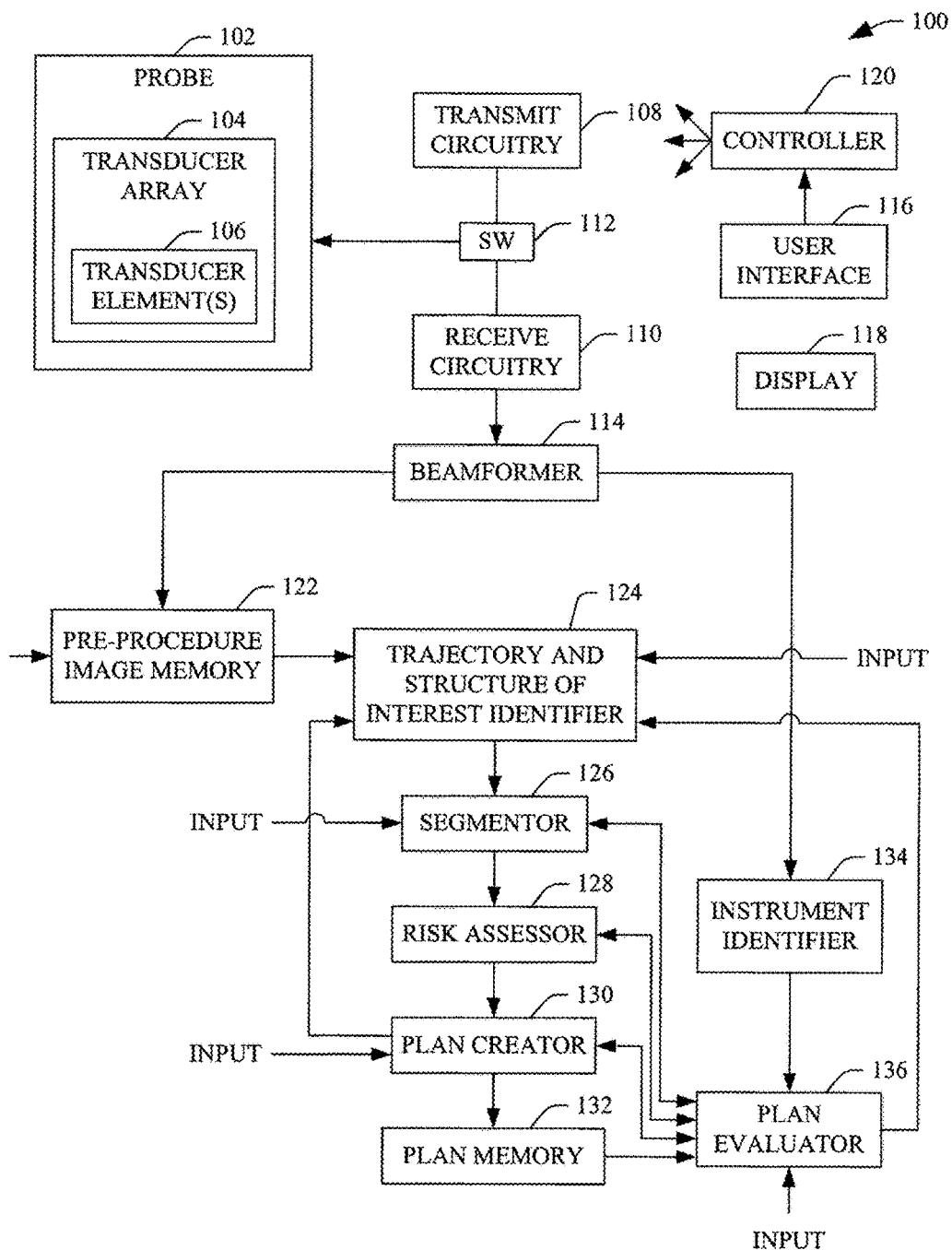
FIG. 1 schematically illustrates an example ultrasound imaging system in connection with procedure planning and evaluation components.

Initially referring to FIG. 1, an ultrasound imaging system 100 includes a probe 102 housing a transducer array 104 having at least one transducer element 106. The at least one transducer element 106 is configured to convert electrical signals to an ultrasound pressured field and vice versa respectively to transmit ultrasound signals into a field of view and receive echo signals, generated in response to interaction with structure in the field of view, from the field of view. The illustrated transducer array 104 can include one or more arrays, including linear, curved (e.g., concave, convex, etc.), circular, etc. arrays, which are fully populated or sparse, etc.

Transmit circuitry 108 generates a set of pulses (or a pulsed signal) that are conveyed, via hardwire (e.g., through a cable) and/or wirelessly, to the transducer array 104. The set of pulses excites a set (i.e., a sub-set or all) of the at least one transducer element 106 to transmit ultrasound signals. Receive circuitry 110 receives a set of echoes (or echo signals) generated in response to a transmitted ultrasound signal interacting with structure in the field of view. A switch (SW) 112 controls whether the transmit circuitry 108 or the receive circuitry 110 is in electrical communication with the at least one transducer element 106 to transmit ultrasound signals or receive echoes.

A beamformer 114 processes the received echoes by applying time delays to echoes, weighting echoes, summing delayed and weighted echoes, and/or otherwise beamforming received echoes, creating beamformed data. In B-mode imaging, the beamformer 114 produces a sequence of focused, coherent echo samples along focused scanlines of a scanplane. The scanplanes correspond to the imaging planes of the transducer array 104. The beamformer 114 may also process the scanlines to lower speckle and/or improve specular reflector delineation via spatial compounding, and/or perform other processing such as FIR filtering, IIR filtering, edge enhancement, etc.

A user interface (UI) 116 includes an input device(s) (e.g., a physical button, a touch screen, etc.) and/or an output device(s) (e.g., a touch screen, etc.), which allow for interaction between a user and the ultrasound imaging system 100. A display 118 is configured to display an image and/or other information. A controller 120 controls one or more of the components 102-114 of the ultrasound imaging system 100. Such control includes controlling one or more of the components to perform the functions described herein and/or other functions.

Pre-procedure image memory 122 stores a pre-procedure image. The memory 122 can be local to the ultrasound imaging system 100, remote therefrom, e.g., memory of a data repository such as a picture arching and communication system (PACS), a radiology information system (RIS), etc., distributed between the ultrasound imaging system 100 and one or more remote memories, etc. The pre-procedure image can include 2-D and/or 3-D image data, and can be generated by the ultrasound imaging system 100, another ultrasound imaging system and/or another imaging modality such as a magnetic resonance imaging (MRI) system, a computed tomography (CT) imaging system, and/or other imaging system.

A trajectory and structure of interest identifier 124 processes the pre-procedure image and identifies a trajectory to a target structure of interest, which represents a path for an instrument (e.g., a needle) to the target structure of interest. In one example, the trajectory is automatically generated in response to an identification of the target structure of interest on the pre-procedure image, which can be identified based on a user input and/or otherwise. In another instance, the trajectory is semi-automatically or manually identified by a user, e.g., via freehand drawing, etc. In either instance, the user can reject, modify or accept the trajectory. In addition, the identifier 124 can recommend candidate trajectories and/or modifications to trajectories.

A segmentor 126 segments other predetermined structure(s) from the pre-procedure image such as one or more structures that are not to be traversed by the identified trajectory. In the context of a tumor biopsy, the other structure may include organs, blood vessels, etc. Such structure(s) can be identified via a user input, a default set of structures for the structure of interest, a clinician customized set of structure, and/or other structure. Known and/or other segmentation algorithms can be employed. The segmentation algorithm can be automatic, semi-automatic or manual. In any instance, the user can reject, modify or accept the segmentation, and/or add a structure to segment and/or remove a segmentation.

A risk assessor 128 processes the pre-procedure image along with the identified trajectory and the segmented other structure(s) and computes a risk for the entire length of the trajectory or multiple risks, each for a sub-segment of the entire trajectory. The risk identifies a risk of contacting the structure and/or otherwise affecting (e.g., damaging, etc.) the structure with the instrument. Known and/or other risk assessment algorithms can be employed. For example, risk can be determined based on distance between the trajectory and the segmented other structure at one or more points along the trajectory. This includes determining different levels of risk for different points along the trajectory one point on the trajectory may be associated with greater risk relative to another point. Additionally or alternatively, the risk is computed based on the area that is affected by the treatment.

A plan creator 130 creates an examination procedure plan based on the pre-procedure image, the identified trajectory, the segmented other structure(s), and the risk. This can be achieved automatically and/or semi-automatically. This may include evaluating the current risk based on a predetermined set of rules, a predetermined risk threshold, etc. to determine if the current risk level is satisfactory. Where the risk level is not satisfactory, the trajectory can be discarded and a new one generated by components 124-128 or modified by a user, e.g., both based on different input and/or processing parameters.

In one instance, the risk information is presented, visually, audibly, etc. for observation. For example, the risk level can be identified through color coding the trajectory and/or a region around the trajectory, e.g., where red represents high risk, yellow represents medium risk and green represents low risk. In an alternative configuration, the risk level is provided as a numerical value in conjunction with a range from low to high risk and optional explanatory text on the image about the trajectory and/or otherwise. Other risk representations are also contemplated herein.

With this information, a user can accept or reject a current trajectory. This may include accepting a trajectory the plan creator 130 recommends to reject, rejecting a trajectory the plan creator 130 recommends to accept, as well as accepting the recommendation of the plan creator 130, where the plan creator 130 is configured to provide a recommendation. Rejection may invoke starting the process over again and/or modifying the existing rejected trajectory.

A plan memory 132 stores accepted plans. One or more of the planning components (122-132) can be part of the system 100 and/or an apparatus separate therefrom.

During a procedure, an instrument identifier 134 processes an intra-procedure real-time image and identifies a location of an instrument therein. As utilized herein, a real-time image refers to a currently or presently generated image, generated from currently or presently acquired data (i.e., ultrasound echoes). In the illustrated example, the real-time image is a real-time ultrasound image, which can be a 2-D and/or a 3-D image. In another embodiment, the real-time image can alternatively or additionally be an MRI, CT, etc. 2-D and/or a 3-D image. Known and/or other risk assessment algorithms can be employed. For example, the instrument can be identified via a tracking device (e.g., an electromagnetic sensor thereon), pixel intensity, a change in pixel intensity, object shape in the image, etc.

A plan evaluator 136 combines (e.g., fuses, registers, overlays, etc.) the intra-procedure real-time image with the location of the instrument identified therein with the pre-procedure image where the previously segmented structure was identified. This can be through a registration algorithm and/or otherwise. From this, the plan evaluator 136 automatically locates current locations of the structure in the real-time image relative to the location of the instrument in the real-time image based on the previously segmented structure and computes a new risk. Similar to planning, the risk can be based on the proximity of the instrument with respect to the identified structure along the trajectory and the risk can be presented and/or evaluated based on rules, thresholds, etc.

Where the risk level is satisfactory, the instrument can be advanced and another real-time image can be generated and evaluated to evaluate the plan. Where the risk level is not satisfactory, in one instance, the procedure is terminated and the planning process is revisited. This may involve removing the instrument and re-scheduling the procedure. In another instance, the plan is instead modified during the procedure, and the procedure is finished. The modification may include changing the trajectory, identifying additional or fewer structures to avoid, etc. For a procedure involving a treatment, once the instrument is guided to the target tissue and the treatment is performed, the plan evaluator 136 can generate a final risk, e.g., to determine an extent of the treatment.

With the configuration described herein, the previously identified structures are automatically located in the intra-procedure real-time image relative the current location of the instrument and real-time trajectory risk is provided. As such, during the procedure the clinician does not have to cognitively assess a risk of injury to neighboring anatomical structures as the needle is inserted and moved in the patient. Furthermore, one or more of the intra-procedure components (134 and 136) can be part of the system 100 and/or an apparatus separate therefrom. Furthermore, the plan evaluator 136 can employ the components 126-130 (as shown in the illustrated example) or have and/or utilize one or more of its own corresponding components.

In the illustrated example, at least one of the components of the system 100 can be implemented via one or more computer processors (e.g., a microprocessor, a control processing unit, a controller, etc.) executing one or more computer readable instructions encoded or embodied on computer readable storage medium (which excludes transitory medium), such as physical computer memory, which causes the one or more computer processors to carry out the various acts and/or other functions and/or acts described herein. Additionally or alternatively, the one or more computer processors can execute instructions carried by transitory medium such as a signal or carrier wave.

Figure 2:
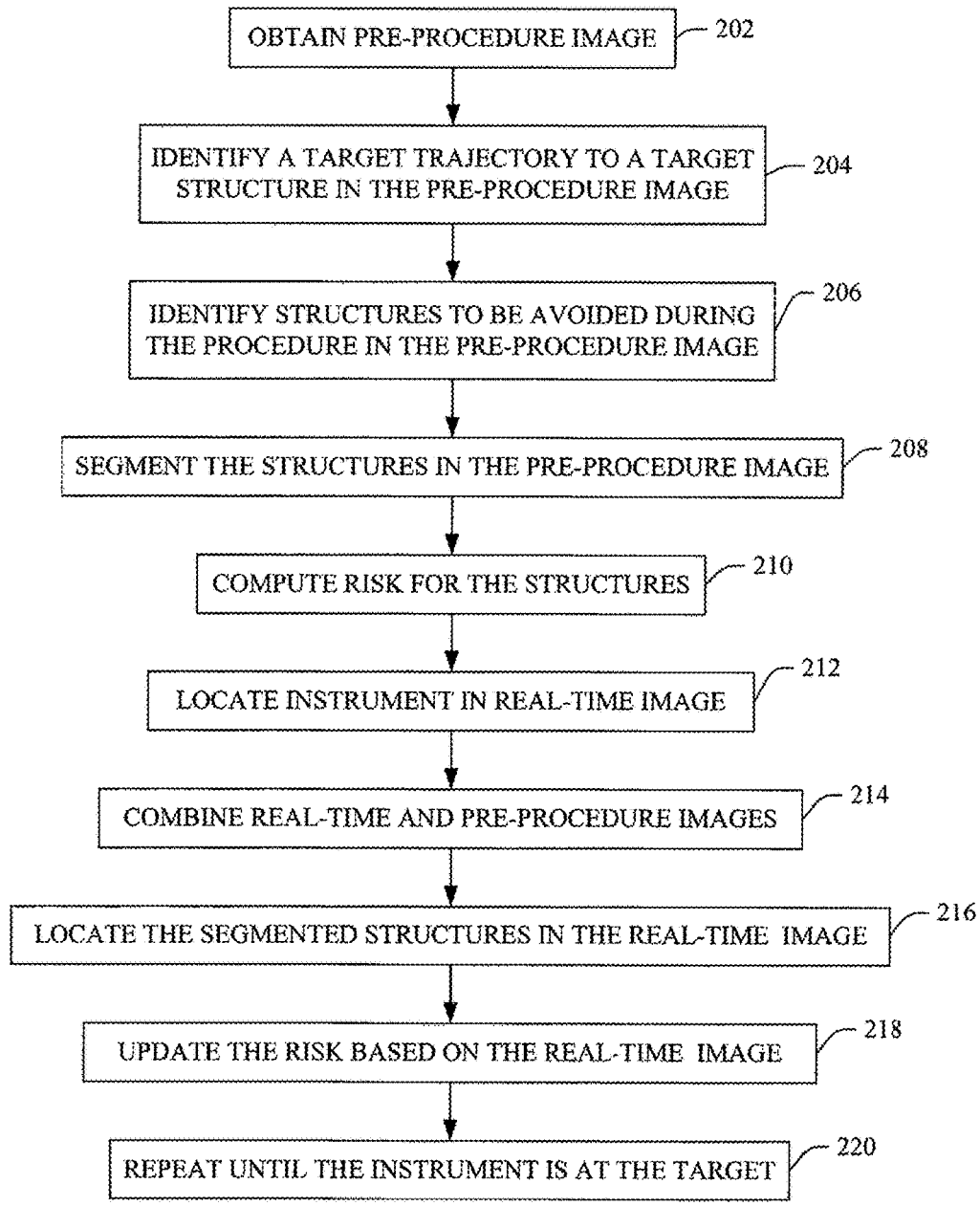
FIG. 2 illustrates an example method in accordance with an embodiment herein.

FIG. 2 illustrates an example method in accordance with an embodiment herein.

It is to be appreciated that the ordering of the above acts is not limiting. As such, other orderings are contemplated herein. In addition, one or more acts may be omitted and/or one or more additional acts may be included.

Figure 3:
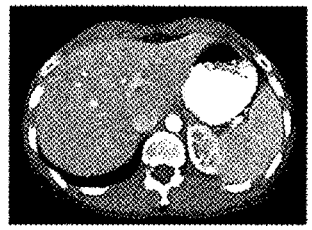
FIG. 3 shows an example pre-operative image.

At 202, a pre-procedure image is obtained, as described herein and/or otherwise. FIG. 3 shows an example pre-procedure image.

Figure 4:
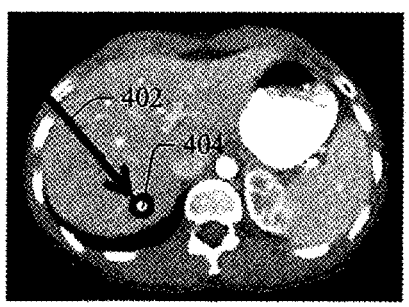
FIG. 4 shows an example trajectory to a target structure in the pre-operative image.

At 204, a target trajectory to a target structure is identified in the pre-procedure image, as described herein and/or otherwise. FIG. 4 shows an example trajectory 402 to a target structure 404.

At 206, structures to be avoided during the procedure are identified in the pre-procedure image, as described herein and/or otherwise.

Figure 5:
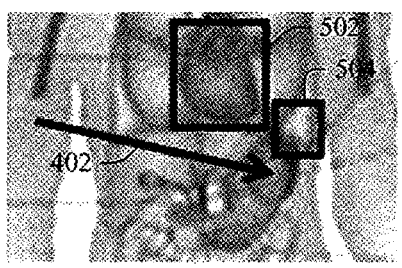
FIG. 5 shows example contours of segmented structures in a pre-operative image.

At 208, the identified structures are segmented in the pre-procedure image, as described herein and/or otherwise. FIG. 5 shows example contours 502 and 504 of such structures.

At 210, a risk is computed for the trajectory 402 and the segmented structures 502 and 504, as described herein and/or otherwise.

Figure 6:
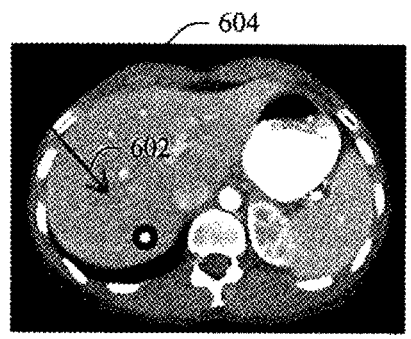
FIG. 6 shows an example instrument location in a real-time image.

At 212, an instrument is located in a real-time intra-procedure image, as described herein and/or otherwise. FIG. 6 shows example in which an instrument 602 is located in a real-time image 604.

At 214, the real-time image is combined with the pre-procedure image where structures were previously identified, as described herein and/or otherwise.

Figure 7:
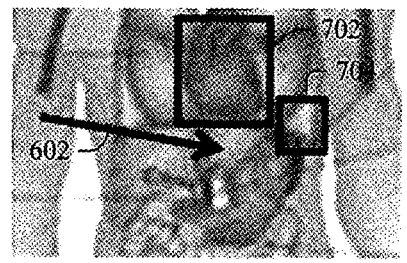
FIG. 7 shows segmented structure in a real-time image relative to the instrument location.

At 216, the segmented structures in the pre-procedure image are located in the real-time image relative to the instrument location, as described herein and/or otherwise. FIG. 7 shows current locations of structure 702 and 704 relative to the current location of the instrument 602.

At 218, the risk is updated based on the real-time image, as described herein and/or otherwise.

At 220, acts 214-218 are repeated for subsequent real-time images until the instrument is at the target, as described herein and/or otherwise.

Optionally, after the procedure at the target, a final risk is computed to determine an extent of treatment.

At least a portion of one or more of the methods discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    receiving an intra-procedure image of a region of interest of an object, wherein the intra-procedure image includes a representation of an instrument in the object;
    identifying a location of the instrument in the object in the intra-procedure image;
    overlaying the intra-procedure image with the identified location of the instrument with a pre-procedure image of the region of interest of the object where a previously segmented anatomical structure to be avoided by the instrument and treatment was identified, wherein the pre-procedure image includes a planned trajectory for the instrument from a surface of the object to a target in the object and the previously segmented anatomical structure;

segmenting, in the intra-procedure image overlaid over the pre-procedure image, a current anatomical structure in the intra-procedure image relative to the instrument by directly using the previously segmented anatomical structure in the overlaid pre-procedure image, wherein the current anatomical structure in the intra-procedure image represents a same physical structure as the previously segmented anatomical structure in the pre-procedure image;

computing a risk of the instrument contacting the physical structure as the instrument moves in the object with the identified location of the instrument, the trajectory, and the segmented current anatomical structure in the intra-procedure image; and presenting the risk.

2. The method of claim 1, wherein the intra-procedure image is an ultrasound image.

3. The method of claim 2, wherein the ultrasound image is a real-time image presently generated from presently acquired ultrasound data.

4. The method of claim 1, wherein the risk is computed based on at least one of a distance between the trajectory and the segmented current anatomical structure in the intra-procedure image and on an area affected by the treatment.

5. The method of claim 4, wherein the risk includes multiple risks, each risk corresponding to a different sub-portion of the trajectory.

6. The method of claim 1, further comprising:
receiving a subsequent intra-procedure image of the region of interest of the object;
identifying a subsequent location of the instrument in the object in the subsequent intra-procedure image;
combining the subsequent intra-procedure image with the pre-procedure image of the region of interest of the object;
segmenting a subsequent anatomical structure in the subsequent intra-procedure image relative to the instrument using the previously segmented anatomical structure in the pre-procedure image from the combined images, wherein the subsequent anatomical structure in the subsequent intra-procedure image represents the same physical structure as the previously segmented anatomical structure in the pre-procedure image; and
computing a subsequent risk of the instrument contacting the physical structure along the trajectory with the identified subsequent location of the instrument, the trajectory, and the segmented subsequent anatomical structure in the subsequent intra-procedure image.

7. The method of claim 1, further comprising:
generating a new trajectory based on the computed risk.

8. The method of claim 1, further comprising:
maintaining the trajectory based on the computed risk.

9. The method of claim 1, further comprising:
recommending termination of a procedure based on the computed risk.

10. The method of claim 1, further comprising:
generating a trajectory for guiding the instrument to the target using the intra-procedure image.

11. The method of claim 1, further comprising:
receiving the pre-procedure image;
identifying the target in the pre-procedure image;
generating the trajectory based on the identified target;
identifying an anatomical structure to be avoided in the pre-procedure image;

segmenting the anatomical structure;
computing a pre-procedure risk of the instrument contacting the physical structure along the trajectory with the trajectory and the segmented anatomical structure in the pre-procedure image; and
creating a procedure plan with the trajectory.

12. The method of claim 11, further comprising:
rejecting the trajectory based on the pre-procedure risk.

13. The method of claim 11, further comprising:
accepting the trajectory based on the pre-procedure risk.

14. The method of claim 1, further comprising:
computing a final risk after completion of a procedure.

15. A computer apparatus, comprising:
an instrument identifier configured to receive a real-time image and identify a position of an instrument in the real-time image;
a segmentor configured to segment a predetermined set of anatomical structures in the real-time image using previously segmented anatomical structures in a previously generated image, after overlaying the real-time image over the previously generated image, in the overlaid real-time image, and directly from the previously segmented anatomical structures in the overlaid previously generated image;
a risk assessor configured to compute a risk of the instrument damaging the anatomical structures from the identified position, the segmented structures in the real-time image, and a planned path for the instrument in the previously generated image; and
a plan evaluator configured to evaluate the plan using the computed risk and present information indicating the risk along the planned path,
wherein the instrument identifier, the segmentor, the risk assessor, and the plan evaluator are implemented with one or more hardware computer processors.

16. The computer apparatus of claim 15, wherein the plan evaluator presents the risk through color coding, and each color indicates a different risk level.

17. The computer apparatus of claim 15, wherein the plan evaluator presents the risk through numerical values, and each numerical value indicates a different risk level.

18. The computer apparatus of claim 15, wherein the plan evaluator updates the risk each time a subsequent real-time image is received.

19. The computer apparatus of claim 15, further comprising:
a transducer array that receives echoes, which are processed to generate the real-time image.

20. A non-transitory computer readable medium comprising processor-executable instructions, that, when executed by a computer processor, are configured to enable a computer processor to:
receive an intra-procedure image of a region of interest of an object, wherein the intra-procedure image includes a representation of an instrument in the object;
identify a location of the instrument in the object in the intra-procedure image;
overlay the intra-procedure image with the identified location of the instrument with a pre-procedure image of the region of interest of the object where a previously segmented anatomical structure to be avoided by the instrument and treatment was identified, wherein the pre-procedure image includes a planned trajectory for the instrument from a surface of the object to a target in the object and the previously segmented anatomical structure;

segment, in the intra-procedure image overlaid over the pre-procedure image, a current anatomical structure in the intra-procedure image relative to the instrument by directly using the previously segmented anatomical structure in the overlaid pre-procedure image, wherein the current anatomical structure in the intra-procedure image represents a same physical structure as the previously segmented anatomical structure in the pre-procedure image;

compute a risk of the instrument contacting the physical structure as the instrument moves in the object with the identified location of the instrument, the trajectory, and the segmented current anatomical structure in the intra-procedure image; and present the risk.

* * * * *